US00PP26828P2

(12) United States Plant Patent
Avent

(10) Patent No.: US PP26,828 P2
(45) Date of Patent: Jun. 14, 2016

(54) ***BAPTISIA* PLANT NAMED 'BLONDE BOMBSHELL'**

(50) Latin Name: ***Baptisia* hybrid**
Varietal Denomination: Blonde Bombshell

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 119 days.

(21) Appl. No.: 14/121,410

(22) Filed: Sep. 2, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of interspecific *Baptisia*, 'Blonde Bombshell', that is characterized by its flowers that are light yellow in color, its compact and upright and slightly mounded plant habit, its flower stems that are held well above the foliage with short internode lengths between flowers, and its heavy blooming habit with numerous flowering stems and numerous flowers per flowering stem.

2 Drawing Sheets

Botanical classification: *Baptisia* hybrid.
Cultivar designation: 'Blonde Bombshell'.

BACKGROUND OF THE INVENTION

The present invention relates to a new and distinct cultivar of hybrid *Baptisia* plant, botanically known as *Baptisia* 'Blonde Bombshell' and will be referred to hereafter by its cultivar name, 'Blonde Bombshell'. The new cultivar represents a new false indigo, an herbaceous perennial grown for landscape use.

The new invention arose from an ongoing breeding program by the Inventor in Raleigh, N.C. The objective of the breeding program is to develop novel interspecific hybrids of *Baptisia* that exhibit good garden performance with tall and upright plant habits and inflorescences that are held well above the foliage.

'Blonde Bombshell' originated as a seedling that arose from seed planted from open pollination of an unnamed plant of *Baptisia shaerocarpa* in April of 2008 in a controlled block of potential pod and seed parents. The male parent is therefore unknown. The new *Baptisia* was selected as a single unique plant in 2008.

Asexual propagation of the new cultivar was first accomplished by shoot tip cuttings in May of 2009 in Raleigh, N.C. under the direction of the Inventor. Asexual propagation by shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Raleigh, N.C. These attributes in combination distinguish 'Blonde Bombshell' as a unique cultivar of *Baptisia*.

1. 'Blonde Bombshell' exhibits flowers that are light yellow in color.
2. 'Blonde Bombshell' exhibits a compact and upright and slightly mounded plant habit.

3. 'Blonde Bombshell' exhibits flower stems that are held well above the foliage with short internode lengths between flowers.
4. 'Blonde Bombshell' exhibits a heavy blooming habit with numerous flowering stems and numerous flowers per flowering stem.

The female parent of 'Blonde Bombshell' differs from 'Blonde Bombshell' in having flowers that are darker yellow in color, fewer flowering stems that are shorter in height with less flowers and greater internode lengths between flowers, and in having a less upright plant habit. 'Blonde Bombshell' can be most closely compared to *Baptisia* cultivars 'Lemon Meringue' (U.S. Plant Pat. No. 24,280) and 'Anne' (not patented). 'Lemon Meringue' is similar to 'Blonde Bombshell' in having yellow flowers and upright flowering stems. 'Lemon Meringue' differs from 'Blonde Bombshell' in having flowering stems that are darker in color with longer internodes between flowers, in having a much wider plant habit, and in blooming 1 to 2 weeks later. 'Anne' is similar to 'Blonde Bombshell' in flower color and season of bloom. 'Anne' differs from 'Blonde Bombshell' in having flowering stems that are darker in color with longer internodes between flowers, in having a much wider plant habit, and in blooming slightly later.

BRIEF DESCRIPTION OF THE DRAWINGS

The accompanying colored photographs illustrate the overall appearance and distinct characteristics of the new *Baptisia*. The photographs were taken of plants four years in age as grown outdoors in a trial garden in Raleigh, N.C.

The photograph in FIG. 1 provides a side view of 'Blonde Bombshell' in bloom and illustrates its plant habit and prolific blooming habit.

Figure 1:
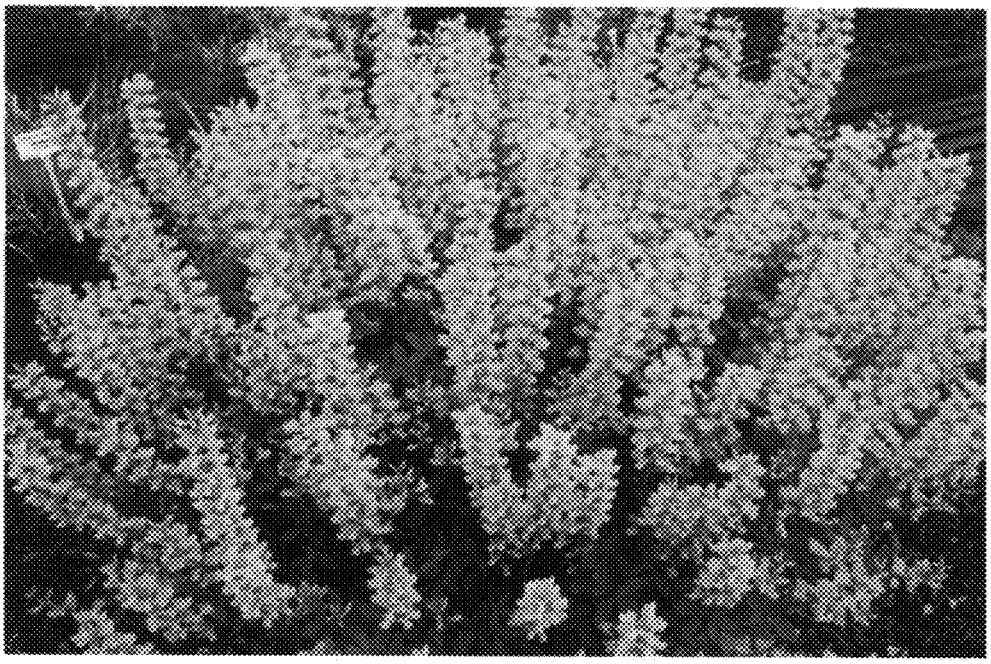
Figure 2:
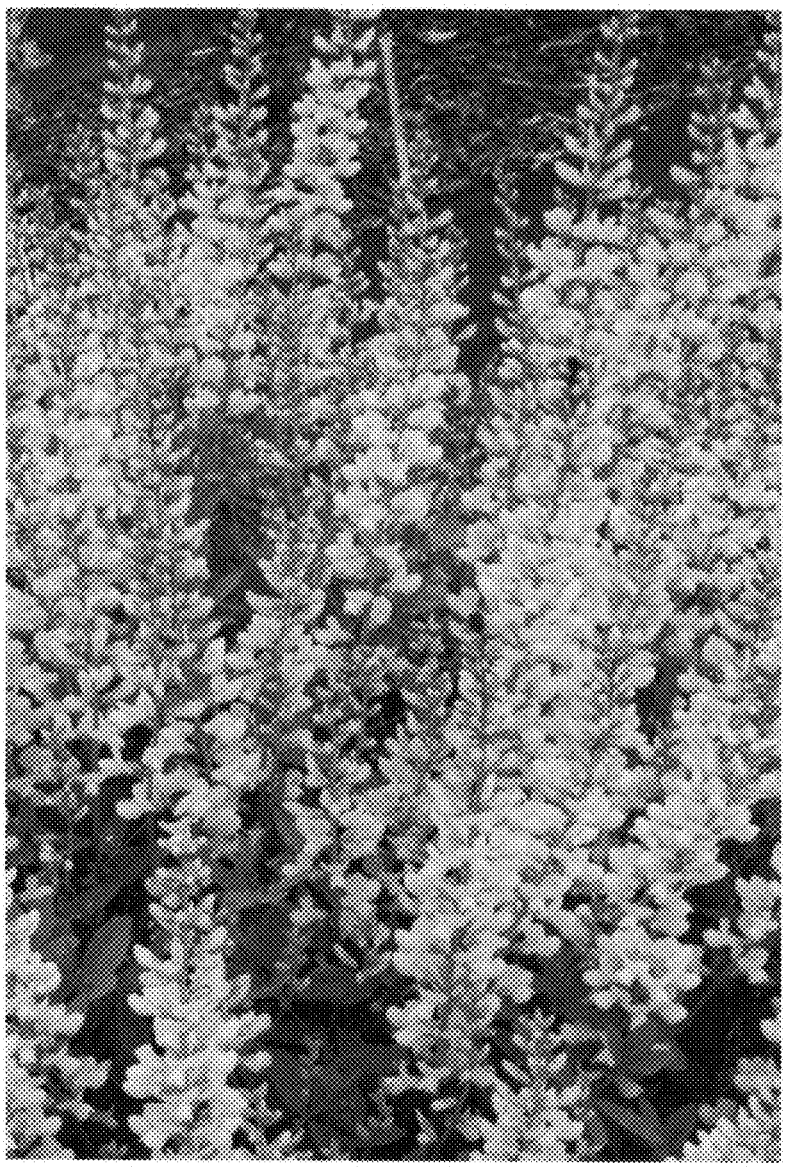

The photograph in FIG. 2 provides a close-up view of the inflorescences.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of seven year-old plants of the new cultivar as grown outdoors in a trial garden in Raleigh, N.C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid April to early May in Raleigh, N.C.

*Plant habit.*—Compact, upright and slightly mounded with inflorescences held well above foliage.

*Height and spread.*—An average of 1 m in height and spread.

*Hardiness.*—At least in U.S.D.A. Zones 4 to 9.

*Diseases.*—No susceptibility to disease has been observed.

*Root description.*—Deep rooted, fleshy.

*Propagation.*—Shoot tip cuttings.

*Growth rate.*—Vigorous.

Stem description:

*Branch habit.*—Densely branched; average of 19 main branches, each with an average of 3 secondary branches, and 2 tertiary branches.

*Stem size.*—Main stem; average of 1.1 m (including peduncle) in length and 8 mm in width, secondary; average of 45 cm in length and 4 mm in width, tertiary; an average of 20 cm in length and 2 mm in width.

*Stem shape.*—Rounded.

*Stem color.*—144A to 144B, a blend of 200A and N199B when seedpods mature.

*Stem surface.*—Glabrous, satiny, and slightly glaucous and lenticellate.

Foliage description:

*Leaf shape.*—Fan-shaped in overall outline.

*Leaf division.*—Ternate.

*Leaf internode.*—Foliage begins 45 cm from base until foliage expands, an average of 10 cm on main stem and an average of 5 cm on secondary branches.

*Leaf size.*—Average 5.1 cm in length and 9 cm in width when mature.

*Leaf quantity.*—About 18 per stem.

*Leaflet shape.*—Oblanceolate to elliptic.

*Leaflet base.*—Cuneate.

*Leaflet apex.*—Acute to rounded.

*Leaflet venation.*—Pinnate pattern, not conspicuous, color matches leaflet color on the upper and lower surface with the mid rib of lower surface 144B.

*Leaflet margins.*—Entire.

*Leaf attachment.*—Petiolate.

*Leaf arrangement.*—Alternate.

*Leaflet surface.*—Glabrous and slightly glaucous on upper and lower surface.

*Leaflet color.*—Newly expanded; upper and lower surface 144A, mature; upper and lower surface a blend of 144A and 138A.

*Leaflet size.*—An average of 4.7 cm in length and 2.2 cm in width.

*Petioles.*—Average of 2.5 mm in length and 1 mm in width, clasping to stem at mature nodes, 144B in color, surface is glabrous and satiny.

*Stipules.*—Lanceolate in shape, base is truncate to stem, apex is narrowly acute to acuminate, up to 5 mm in length and 1 mm in width on mature leaves, 138A in color on upper and lower surface.

Flower description:

*Inflorescence type.*—Terminal racemes of pea-like flowers on main and secondary branches, blooms from the base to the apex.

*Inflorescence size.*—Average of 35 cm in length and 5 cm in width at apex.

*Lastingness of inflorescence.*—About 20 days.

*Flower size.*—About 2.2 cm in depth and about 1.2 cm in diameter.

*Flower fragrance.*—Faint.

*Flower number per inflorescence.*—About 60.

*Peduncle.*—Rounded in shape, up to 40 cm in length and an average of 4.5 mm in width, 144B in color, surface is glabrous, satiny, and slightly glaucous, flower internode length averages 1 cm.

*Petiole.*—About 4 mm in length, about 1 mm in width, oval in shape, 144B in color, glabrous and satiny surface.

*Flower buds.*—Kidney-shaped, about 1.8 cm in length and 7 mm in width, petal portion is 4B in color, calyx portion same as open flowers.

*Flower type*—Papilionaceous, held at about a 45° angle.

*Calyx.*—Campanulate, about 7 mm in length and 5 mm in diameter, surface is glabrous and satiny, N144A in color, persistent.

*Sepals.*—5, fused with the exception of apex of each, free portion is triangular in shape, 2.5 mm in width and depth with an acute apex, color N144A, surface is glabrous on both surfaces.

*Corolla features.*—Papilionaceous (4 segments) with a moderately reflexed banner, 2 lateral wings and a concealed keel, lateral wings; oblong (slightly oblique) in shape, about 1.7 cm in length and 8 mm in width, color on outer surface and the inner surface on the lower portion is 4B, rounded apex, oblique base, keel; not visible, comprised of 2 segments surrounding reproductive organs, oblong (slightly oblique) in shape with rounded apex and oblique base, 1.3 cm in length and 7 mm in width, upper surface and lower surface are 4B in color, segments joined at center point, banner; orbicular in shape, about 1.8 cm in length and 1.7 cm in width, color on outer surface and the inner surface is 4B, apex is rounded with a single notch, surface is glabrous on all sections.

*Receptacle.*—Disk-shaped, gelatinous, 137B in color, about 2 mm in diameter and 1.5 mm in depth.

Reproductive organs:

*Gynoecium.*—1 Pistil, about 1 cm in length, 1 mm in width; style is 145D in color and 1 cm in length; stigma minute, too small to read color, ovary is superior with a stipe, 144A in color, 4.5 mm in length and 2 mm in width; stipe is 145D in color, 2 mm in length and 1 mm in width.

*Androcoecium.*—10 stamens, not united, 2 cm in length and 1 mm in width; filament is 1 cm in length, 1 mm in width and 145B in color; anther is dorsifixed, 1 mm in length and 1 mm in width and 161B in color, pollen is moderate in quantity and 14B in color.

*Fruit.*—An inflated pod, technically a legume, average of 18 produced per inflorescence, Globose and very slightly oblong in shape, average of 1.5 cm in length by 1.3 cm in width with a beak an average of 2 mm in length, color of outer surface when mature is 200A and blushed with N200B, color of inner surface when mature is a blend of N199A and N200A, walls 1.5 mm and hard at maturity, seed; average of 6 per fruit, N199C to N199D in color, oval with the hilum side more or less straight, 4 mm in length, 3 mm in width and 2 mm in thickness.

It is claimed:

1. A new and distinct cultivar of *Baptisia* plant named 'Blonde Bombshell' as herein illustrated and described.

* * * * *